United States Patent [19]
Hoover

[11] Patent Number: 6,162,183
[45] Date of Patent: Dec. 19, 2000

[54] RESPIRATION FEEDBACK MONITOR SYSTEM

[75] Inventor: Jan C. Hoover, Bainbridge, Wash.

[73] Assignee: J&J Engineering, Poulsbo, Wash.

[21] Appl. No.: 09/243,094

[22] Filed: Feb. 2, 1999

[51] Int. Cl.$^7$ .................................................. A61B 5/08
[52] U.S. Cl. ........................................ 600/534; 600/538
[58] Field of Search .................................. 600/534, 531, 600/529, 535, 595

[56] References Cited

U.S. PATENT DOCUMENTS

| | | |
|---|---|---|
| 4,033,332 | 7/1977 | Hardway, Jr. et al. . |
| 4,838,279 | 6/1989 | Fore .......................................... 600/534 |
| 4,909,260 | 3/1990 | Salem et al. . |
| 4,989,612 | 2/1991 | Fore .......................................... 600/534 |
| 5,107,846 | 4/1992 | Atlas ......................................... 600/534 |
| 5,295,490 | 3/1994 | Dodakian ................................. 600/534 |
| 5,400,012 | 3/1995 | Walton ................................... 340/573.1 |
| 5,611,349 | 3/1997 | Halleck et al. ........................... 600/534 |
| 5,615,688 | 4/1997 | O'Dwyer .................................. 600/534 |
| 5,864,291 | 1/1999 | Walton ................................... 340/573.1 |

*Primary Examiner*—Cary O'Connor
*Assistant Examiner*—Navin Natnithithada
*Attorney, Agent, or Firm*—David V. Carlson; Brian L. Johnson; Seed IP Law Group PLLC

[57] ABSTRACT

A system to monitor respiration activity of a user and provide appropriate feedback to the user includes a respiration feedback monitor sized and configured to be worn by the user. In the depicted embodiment, respiration activity is measured with components including a retractable cord coupled to an optical distance measurement device. Feedback is typically provided using vibrations of certain duration and repetition. The system operates under various user selectable operational modes. Each operational mode is associated with particular respiration feedback criteria used to determine appropriate feedback for the user. The respiration feedback criteria is related to respiration rate levels and respiration depth associated with respiration activity level measured for the user. Distribution plots such as histograms associated with respiration measurement contribute to aspects of the feedback criteria and help establish other aspects of appropriate feedback. The depicted embodiment includes a computer interface allowing respiration data recorded by the respiration feedback monitor to be sent to a computer system. The computer system is also used to adjust and download desired operational modes into the respiration feedback monitor.

28 Claims, 6 Drawing Sheets

RESPIRATION FEEDBACK MONITOR SYSTEM

TECHNICAL FIELD

The invention relates to physiological monitoring systems and, more particularly, to a wearable respiration feedback monitor system. The present invention is related to commonly assigned, concurrently filed and co-pending U.S. application U.S. application Ser. No. 09/252,606 for ELECTROMYOGRAPHIC FEEDBACK MONITOR SYSTEM, now issued as U.S. Pat. No. 6,076,011; and U.S. application Ser. No. 09/243,230 for HEART RATE VARIABILITY FEEDBACK MONITOR SYSTEM.

BACKGROUND OF THE INVENTION

Measured breath patterns of an individual's respiration indicate levels of fitness and health. In turn, respiration patterns also influence fitness and health of the individual. Two components of the measured respiration patterns are respiration rate and respiration depth. Respiration rate is a measure of the number of breaths taken per unit time, typically measured in breaths per minute. Respiration depth is a measure of the extent to which an individual's lungs expand, typically measured with air bladders or piezoelectric sensors.

Many specific health and fitness conditions correlate to particular breath patterns involving respiration rate and respiration depth. For instance, activities involving concentration by, or stress on, an individual may result in health problems. Studies have shown that certain individuals do not breath properly when under stress or when concentrating. These individuals are unaware while concentrating or under stress that their respiration is improper. Fortunately, this improper respiration has discernable patterns. For example, oftentimes the improper respiration includes too shallow or infrequent breaths.

Sleep is another area in which measured respiration patterns can be used to give timely feedback to help improve health and fitness conditions including sleep apnea, where the individual can be deprived of oxygen. Those that breath properly during sleep have certain respiration patterns, whereas those that breath improperly during sleep have other respiration patterns both involving respiration rate and depth. Another situation where respiration patterns correlate to health and fitness conditions involves anxiety. Here individuals generally take rapid, shallow breaths during their period of anxiety. Slower, deeper breaths help individuals relax and diminish their anxiety.

If individuals were aware of their respiration patterns throughout the day and night, this information could help them improve their breathing habits. Attempts have been made in the prior art to monitor respirations to a limited extent and to provide a form of feedback to the individual whose respiration is being monitored. Unfortunately, these prior art devices are limited in their monitoring capabilities and scope of application and are not conducive for use during normal activities throughout the day and night by an individual. Prior art devices which monitor respiration and provide feedback burden the users and furnish inadequate feedback. Portable units are limited to measuring respiration rate which is only part of the respiration patterns, so any feedback provided is of limited value. Other sophisticated prior art measuring systems are limited to fixed locations usually involving clinics, hospitals or sophisticated training centers, placing further demands upon individuals attempting to improve their breathing behavior.

For instance, U.S. Pat. No. 4,909,260 to Salem et al. teaches a prior art portable respiration monitor. However, the monitor of Salem is too bulky and cumbersome to be used in many common activities during the day and night. As with other prior art devices, the feedback mechanism of Salem is visual, which requires uninterrupted observation. Also, feedback involved with the prior art systems is not as discreet as desirable for many situations throughout the day and night. Further, the feedback used in the prior art systems is indirectly associated with the monitored condition so does not provide the type of demonstrative and meaningful feedback to dramatically encourage positive changes in behavior by the users. The respiration monitor of Salem requires a sacrifice in lifestyle, wardrobe, and activities in order to use the monitor. The monitor also, like other prior art devices, only measures respiration rate. Respiration rate is only part of the overall respiration patterns that can be used to improve health and fitness of an individual. The prior art systems are clearly inadequate and too burdensome to effectively assist individuals in improving their breathing behavior.

SUMMARY OF THE INVENTION

The invention overcomes the limitations of the prior art and provides additional benefits by providing a respiration feedback monitor system. The respiration feedback monitor allows for expanded accessibility under a wide range of activities. As part of the feedback provided, the respiration feedback monitor furnishes effective feedback that is directly related to areas of concern. The feedback is also discreet in nature. This in addition to other aspects of the invention provides effective, discreet, and timely heart rate variability monitoring and feedback without being overly burdensome. Thus, the invention overcomes the problems and difficulties posed by prior art systems and provides numerous additional benefits.

Aspects of the invention are directed to a respiration feedback monitor system for a user. An aspect of the invention includes a housing sized and configured to be worn by a user, and a vibration output device configured to transmit a vibration signal perceptible by the user when the vibration output is activated. A flexible or non-rigid member configured to extend and retract with respect to at least a portion of the housing, corresponds to respiration of the user. A signal generator affixed to the housing is configured to generate distance signals indicating a distance relating to the extension and retraction of the non-rigid member. A memory is configured to store respiration feedback criteria. A processor affixed to the housing is coupled to the memory, the vibration output device and the signal generator. The processor is configured to receive the distance signals and to turn on the vibration output device based on whether the distance signals satisfy the stored respiration feedback criteria.

In another aspect of the invention, a mode switch allows the user to select an operation mode having a particular respiration feedback criteria from several operational modes under which the processor operates. The processor is further configured to adjust the respiration feedback criteria of the selected operational mode based on the distance signals. The operational modes include Percent Time Amplitude Mode, Threshold Amplitude Mode, Media Frequency Mode, Prompted Exercise Mode, or Current Breath Frequency Mode. In a further aspect of the invention, a connector is configured to detachably connect the respiration feedback monitor system to a computer system via an interface cable wherein the computer system transmits respiration feedback criteria to the respiration feedback monitor system. The processor and memory are monolithically integrated on the same integrated circuit. The respiration feedback criteria is also associated with a threshold, tracking an average, or using a distribution plot. The processor is further configured to turn on the vibration output device based on present correlation results compared with past correlation results wherein the past and present correlation results are based on correlations of a distribution plot of values associated with the distance signals correlated with an ideal distribution plot.

Figure 1C:
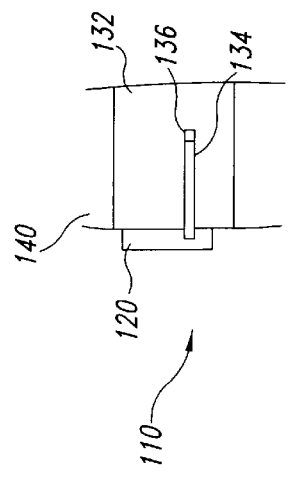
FIGS. 1B and 1C illustrate side views of the embodiment in use.

As is conventional in the field of electrical circuit representation, sizes of electrical components are not drawn to scale and various components are enlarged or reduced to improve drawing legibility. Component details have been abstracted in the Figures to exclude detail such as position of components and certain precise connections used between components.

DETAILED DESCRIPTION OF THE INVENTION

A feedback monitor, and in particular, an apparatus and corresponding method for a respiration feedback monitor system for monitoring respiration activity of a user is described in detail below. In the following description, numerous specific details are provided, such as specific configuration of the apparatus, circuit components, ways of wearing the respiration feedback monitor, respiration criteria used for feedback, etc., to provide a thorough understanding of the embodiments of the invention. One skilled in the relevant art, however, will recognize that the invention can be practiced without one or more of the specific details or with other processes, configurations, and operations etc. In other instances, well-known structures or operations are not shown or described in detail to avoid obscuring the description of the embodiments.

Each of the circuits whose function and interconnection is described in connection with FIGS. 1–4 is of a type known in the art, and one skilled in the art would be able to use such circuits in the described combination to practice the invention. The internal details of these particular circuits are not part of, nor critical to, the invention. Therefore, a detailed description of the internal circuit operation is not required. Similarly, each of the steps depicted in FIGS. 5A and 5B are of a type well known in the art and may itself include a sequence of operations which need not be described herein.

The depicted embodiment of the invention solves problems of prior art respiration monitors. Prior art respiration feedback monitors are burdensome to use and provide insufficient feedback. The depicted embodiment is lightweight and compact, and along with other characteristics, can be worn throughout the day and night in common activities without sacrifice to lifestyle, wardrobe, or activities. Also, the depicted embodiment is simple to operate, which promotes ease of use. Further, the depicted embodiment has a tactile feedback mechanism that is discreet, allowing use of the respiration feedback monitor in most situations and environments common to everyday life. The feedback mechanism does not require attention to be directed toward the feedback mechanism while the users wait for feedback. Direct feedback is applied to the region of concern on a user. This dramatically increases the amount of positive feedback to the user by directly associating the feedback stimulus with the region of concern on the user's body. All these features of the depicted embodiment are in sharp contrast to prior art systems which are limited to certain locations, environments, activities, or other aspects of lifestyle and also do not monitor full respiration patterns nor provide direct feedback. Given the ease of use and great range of locations and environments in which the depicted embodiment can be used, users are afforded the appropriate amount of feedback regarding respiration patterns associated with their activities to allow them to take measures to correct or improve health and fitness conditions.

Figure 1A:
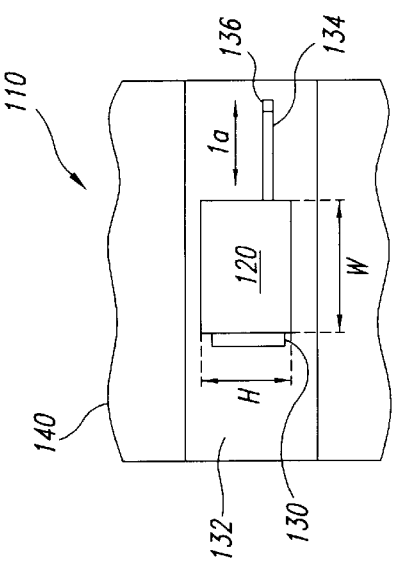
FIG. 1A illustrates a front view of an embodiment of the invention in use.
Figure 1B:
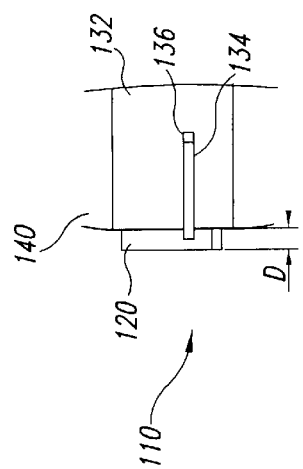

In order to monitor respiration patterns continually, the user ideally should wear a respiration feedback monitor that does not significantly detract from their normal activities throughout the day, nor significantly impact any other aspect of his or her lifestyle. In this way, the respiration feedback monitor travels with the user, rather than the user having to travel to the respiration feedback monitor. The depicted embodiment is small and lightweight enough to be wearable in many positions, locations, and configurations. In the depicted embodiment, a respiration feedback monitor 110 includes a housing 120, as shown in FIG. 1A. A strip 130 is made of hook and loop type fabric, such as fabric identified by the Velcro trademark. The strip 130 is used to help secure the respiration feedback monitor to an elastic bandage 132 which is wrapped around the torso of a user 140, as shown in FIGS. 1A, 1B, and 1C. The location of the feedback monitor 110 is generally in the region of the user 140 that expands and contracts when the diaphragm of the user expands and contracts. The respiration feedback monitor 110 is worn next to or on the elastic bandage 132 and under the clothes of the user 140 to monitor respiration activity of the user. The respiration feedback monitor 110 can thus be worn unobtrusively during normal activities. The respiration feedback monitor 110 in other embodiments is secured to the user 140 through the use of clothing or is worn over clothing either in addition to or separate from the strip 130 and elastic bandage 132. One skilled in the art will recognize that there are many ways to wear the respiration feedback monitor 110 given its small, compact size. The size of the housing is small, such as about 1 to 4 inches or smaller in height (H on FIG. 1A) and about 2 to 5 inches or smaller in width (W on FIG. 1A) and about ½ to 2 inches or smaller in depth (D on FIG. 1B). Preferably, the housing is sized about 2 inches in height, about 3 inches in width and about ½ inch in depth. The housing size greatly contributes to the wearability of the respiration feedback monitor 110. The ways depicted in the present embodiments are not intended to be limited in any way as to how the respiration feedback monitor 110 is to be worn.

As the user 140 exhales and inhales during respiration, a cord 134 retracts into the housing 120 and extends out of the housing 120, respectively. The cord 134 is affixed to the elastic bandage 132 or clothing of the user with a fastener 136 to facilitate correspondence between retraction and extension of the cord and respiration of the user 140. This retraction and extension is shown schematically in FIGS. 1B and 1C, respectively, and is due to the user's torso contracting and expanding as the user's lungs are emptying and filling with air.

Figure 2:
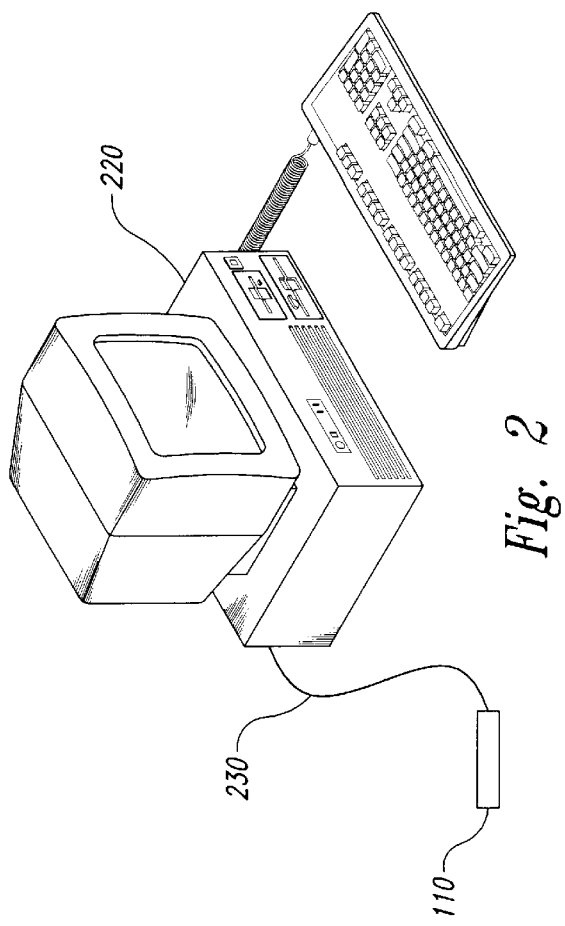
FIG. 2 illustrates the embodiment of FIG. 1 connected to a computer system.

As discussed below, the respiration feedback monitor 110 communicates with a computer system 220 over a computer interface cable 230, shown in FIG. 2. One end of the computer interface cable 230 has an optical isolation module that provides electrical safety and connection compatibility with a communication port of the computer system 220. Alternative embodiments use other communication links instead of the computer interface cable 230. These other communication links include wireless links or optical fiber links. The computer system 220 is used to program the respiration feedback monitor 110 and also to analyze historical data stored in the respiration feedback monitor related to respiration activity of a user such as the user 140. The computer system 220 is thus used to track progress regarding therapeutic intervention or treatment associated with training. Based on the extent of the progress the user experiences, a therapist in the depicted embodiment will adjust or replace criteria used by the respiration feedback monitor 110 to train the user 140 as explained further below. Connection with a computer system 220 via the computer interface cable 230 is typically only an occasional event. More typically, the user 140 frequently wears the respiration feedback monitor 110 without the respiration feedback monitor being connected to any other type of device.

The computer system 220 executes software that provides several capabilities. The software allows a particular feedback mode to be associated with a respiration feedback monitor control setting and thus the levels or thresholds and other parameters may be selected for that particular mode. The software can read respiration signal data collected by the computer system 220 from the respiration feedback monitor 110 and cause the data to be displayed, such as in graph form, on a display or printer of the computer system 220. The software can also store the respiration signal data to appropriate patient/user record files. The software can recall previously stored respiration signal data and produce summary reports of training progress. The software allows visual feedback if the respiration signals are provided to the computer system 220 live by the user 140. This is used to educate the user 140 regarding various feedback vibration patterns and associated criteria for each mode. The software can also provide training information regarding use of the respiration feedback monitor 110.

The respiration feedback monitor 110 also includes a system and method for measuring how the cord 134 moves with respect to the housing 120. The cord 134 is typically one that has high tensile strength with low surface friction such as found with cord used for fishing line or produced from synthetic materials. However, the depicted embodiment is not limited to any particular type of cord. Instead, it is contemplated that any non-rigid member of appropriate dimensions, tensile strength, and properties of friction would be suitable in an embodiment of the invention.

Figure 3:
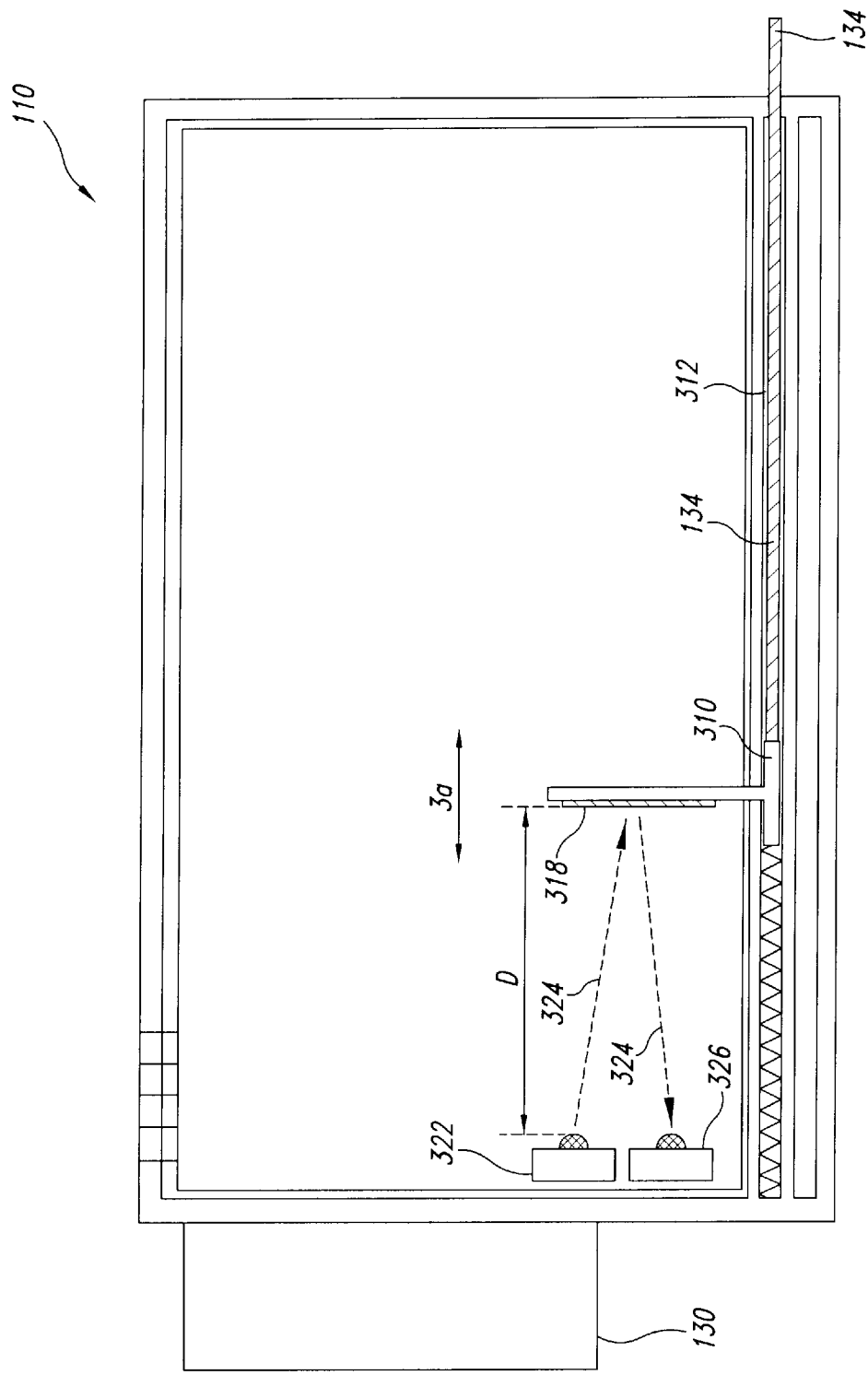
FIG. 3 illustrates operational details of the embodiment of FIG. 1 regarding breath measurement.

Referring to FIG. 3, a support 310 is connected to the cord 134 so that as the cord extends out of the housing 120 or retracts back into the housing, the support 310 slides along an elongated track 312 integral to the housing 120. A spring 314 affixed to a portion of the housing 120 and the support 310 furnishes sufficient force to retract the cord 134 into the housing when the cord becomes slack.

A reflector 318 is attached to, and extends perpendicularly from, the support 310 as shown in FIG. 3. An infrared emitter 322 positioned opposite from the reflector 318 transmits infrared light 324 toward the reflector, which reflects the infrared light toward an infrared detector 326 positioned next to the emitter. As the cord 134 retracts into the housing 120 and extends out of the housing, the support 310 moves along the track 312 causing a distance D between the reflector 318 and the infrared detector 326 to become smaller or larger, respectively. As the distance D becomes larger, the infrared light 324 detected by the infrared detector 326 becomes weaker in intensity. As the distance D becomes smaller, the infrared light detected by the infrared detector 326 becomes greater in intensity.

In general, for the depicted embodiment, the intensity of the infrared light 324 detected by the infrared detector 326 is related to the distance D by $1/D^2$. This relationship is used by the respiration feedback monitor 110 to determine breath patterns of the user 140, including respiration rate and respiration depth, as discussed below. As the user 140 breathes, the distance D changes in direct correlation to the degree of expansion and contraction of the diaphragm of the user, when the respiration monitor 110 is positioned in the diaphragm area of the user. The depicted embodiment uses infrared light, however, the invention is not limited to particular frequencies of visible or non-visible light. Instead, other frequencies of visible and non-visible light may be used in alternative embodiments of the invention. Infrared light is used in the depicted embodiment because of known efficiencies of infrared light emitters. Efficient emitters reduce power requirements, which impact size constraints.

Some of the infrared detectors known in the art have built-in filters that screen out frequencies other than infrared. The filters help to reduce error introduced by ambient lighting levels found in different environments including those having bright sunlight and those having dimly lit artificial light. While the depicted embodiment uses the reflector 318, other embodiments rely on direct transmission of light, for example, by placing light emitter 322 on the support 310 and directed toward the light detector 326.

Figure 4A:
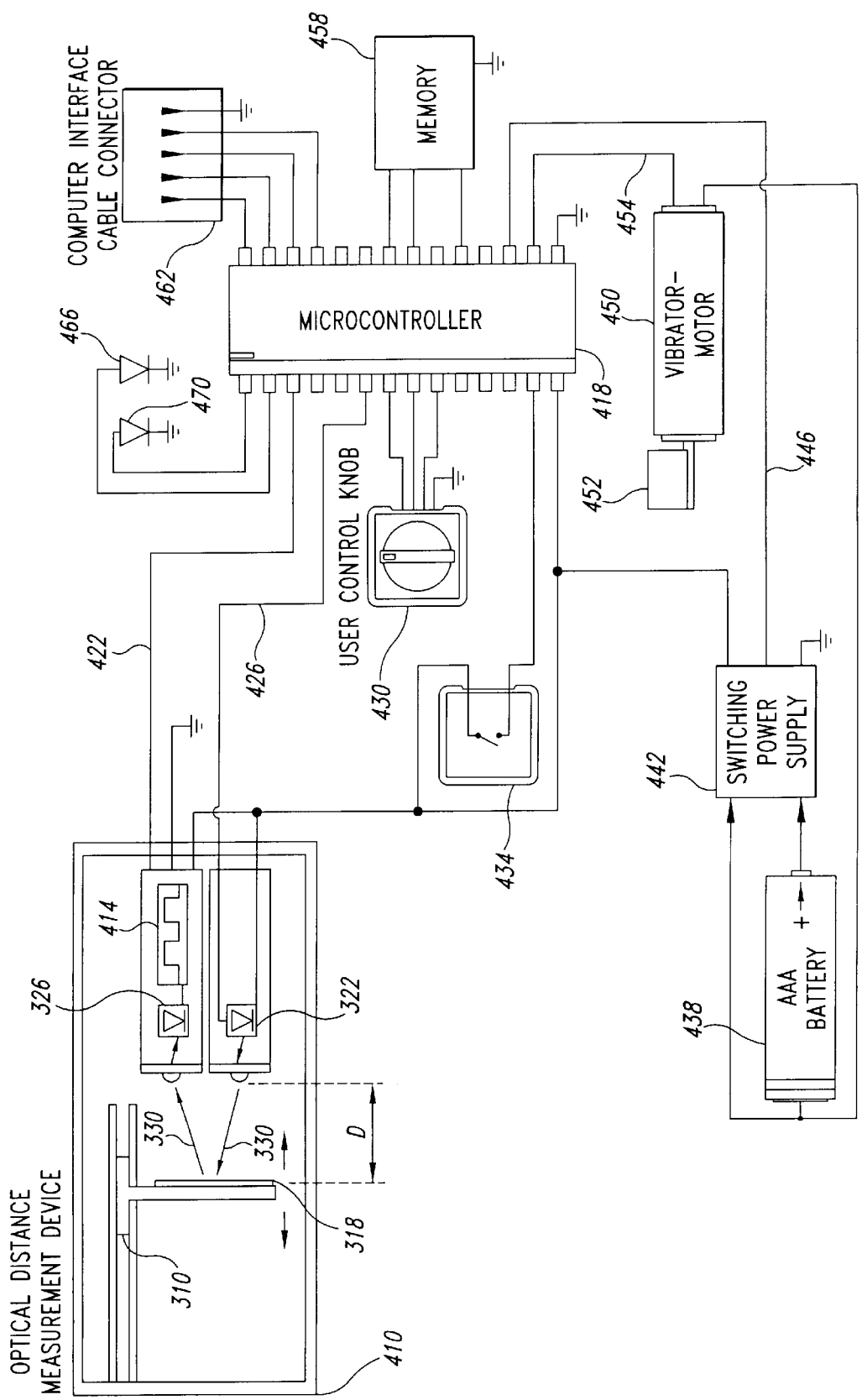
FIG. 4A is a block diagram of the electronic components involved with the embodiment of FIG. 1.
Figure 5A:
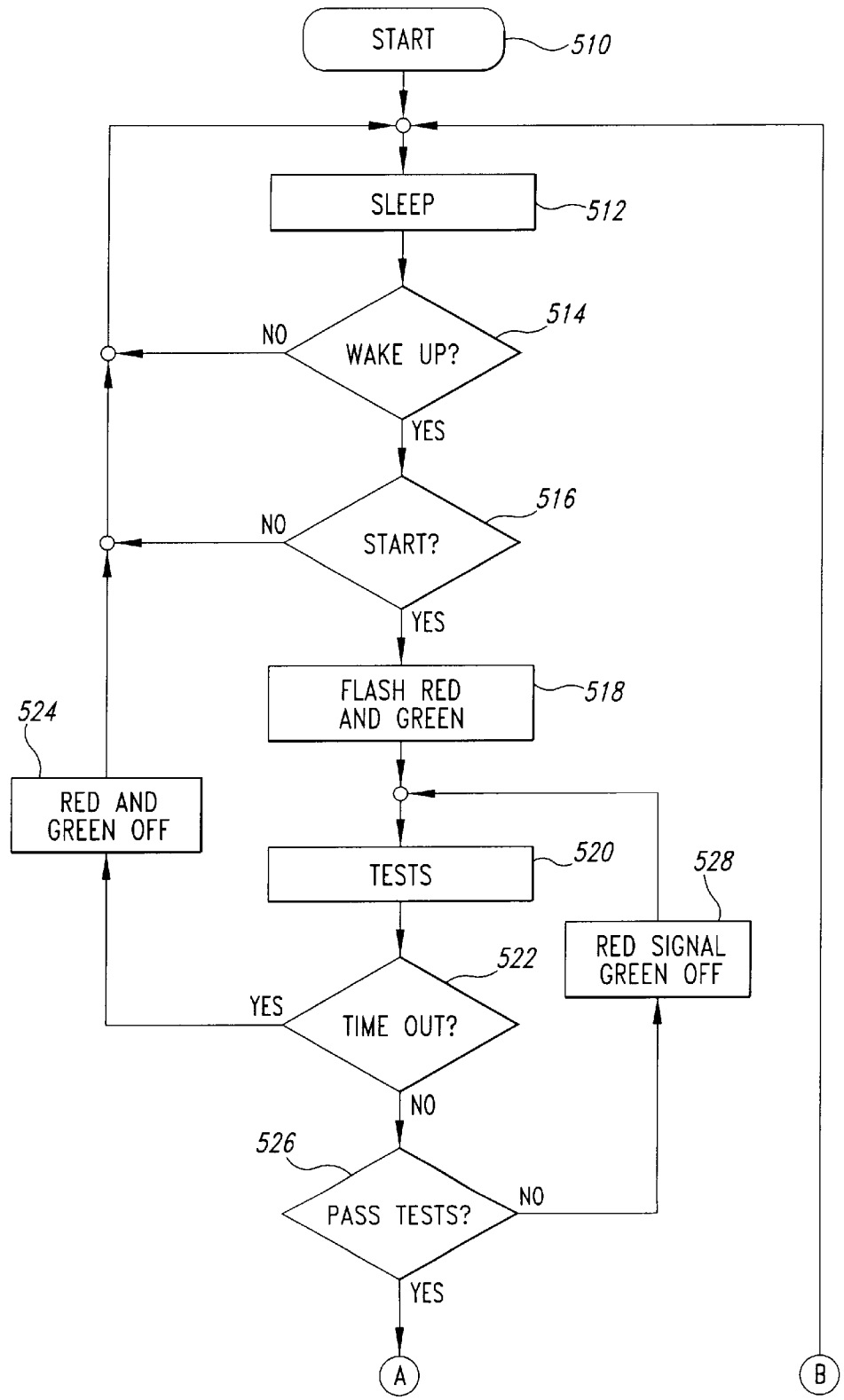
FIGS. 5A and 5B show a flow chart of a method utilized by the embodiment of FIG. 1.
Figure 5B:
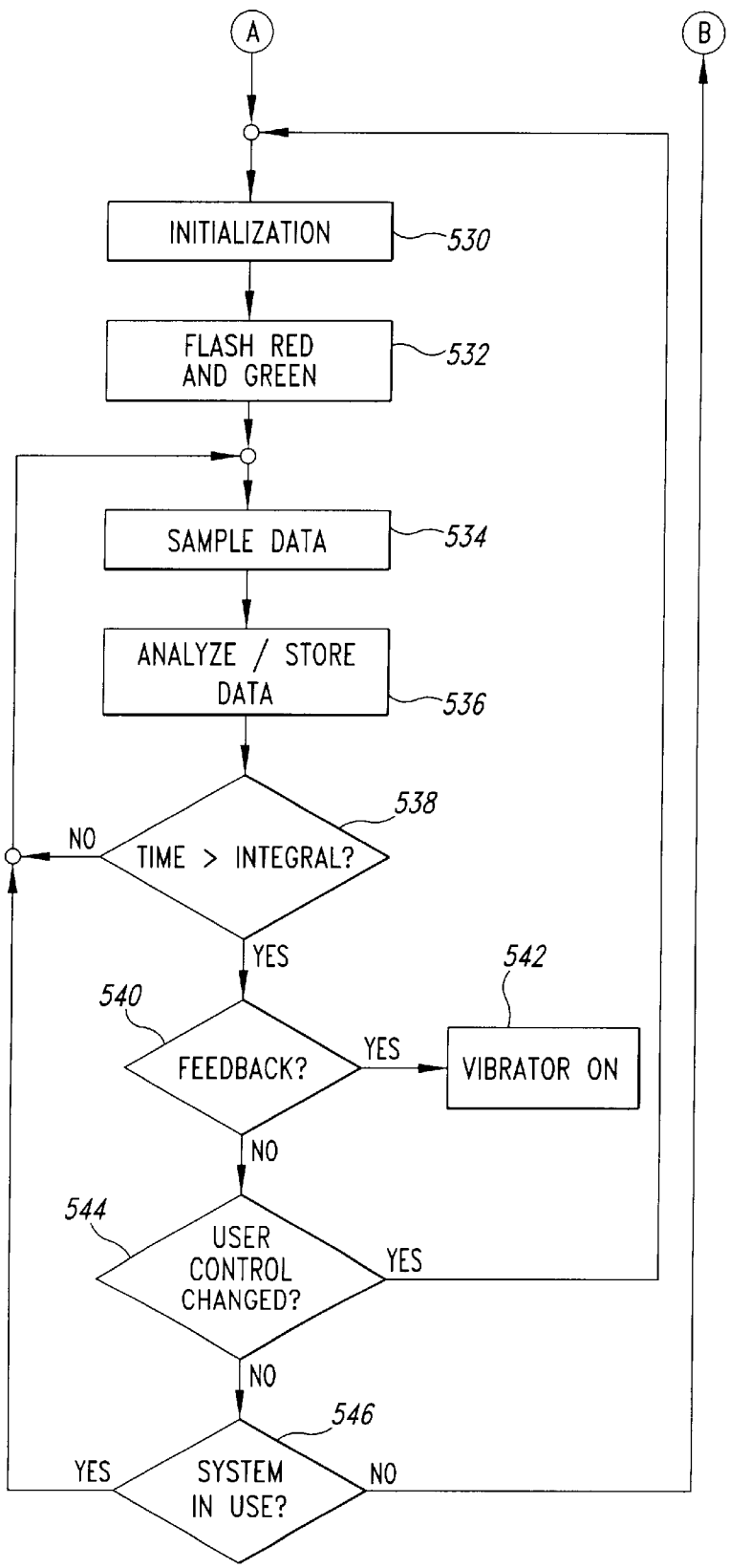

Further components of the respiration feedback monitor 110 for the depicted embodiment are shown in FIG. 4A. Included in these components is an optical distance measurement device 410 that generates a form of respiration signals, namely, distance signals based on distance measurements. The optical measurement device 410 includes support 310, reflector 318, infrared emitter 322, and infrared detector 326. The optical measurement device 410 also includes a light-to-frequency converter 414 that converts the infrared light 324 detected by the infrared detector 326 into an electrical oscillating electrical signal with an output frequency proportional to the square root of the intensity of the infrared light detected by the infrared detector. The depicted embodiment uses an oscillating electrical signal having the form of a square-wave. The square-wave signal repeats a characteristic shape for a period of time $T_{SW}$. The characteristic shape of the square-wave signal includes a constant negative voltage value for a portion of $T_{SW}$ and a constant positive voltage value for another portion of $T_{SW}$. The remaining brief portions of $T_{SW}$ are associated with the square-wave signal transitioning between the constant negative and positive values. The value for the time period is $T_{SW}$ is inversely related to the frequency of the square-wave signal.

Alternative embodiments use other forms of oscillating electrical signals. All the oscillating electrical signals used have forms conducive to measuring their signal frequencies and associated time periods. The light-to-frequency converter 414 in this regard acts as a signal generator that generates distance signals representative of the extent of expansion or contraction of the user's diaphragm or chest as respiration occurs.

Further embodiments utilize other transducers that convert the user's movement of expansion and contraction of their diaphragm or chest into a signal. For instance, one embodiment uses ridged members that are hingedly connected. A transducer is located at the hinge point of the hingedly connected rigid members to convert the rotational motion of the hinge caused by the user's respiration into an electrical signal.

A microcontroller 418 receives the square-wave signal from the optical measurement device 410 over an output frequency line 422. The microcontroller 418 is a particular form of processor as described below, however, other embodiments of the invention use other forms of processors to accomplish the described objectives. In the depicted embodiment, the optical measurement device 410 and the microcontroller 524 are typically located in the same housing 120. However, in other embodiments, the optical measurement device 410 and the microcontroller 524 are housed in separate structures and linked through a data link, such as an electrical, optical or wireless link. The microcontroller 418 turns the optical measurement device 410 on and off through an emitter power line 426. To measure the period of the oscillating square-wave signal generated by the light-to-frequency converter 414, the microcontroller 418 turns on the emitter power for a period of time and enables an internal timer. Each rising edge of the square-wave signal from the light-to-frequency converter 414 generates an interrupt signal resetting the internal timer and causing the microcontroller 418 to store the time counted by the timer in an internal 16 bit register. This stored timing data is then used by the microcontroller 418 to determine the period of the square-wave signal from the light-to-frequency converter 414. As stated, the frequency of the square-wave signal is proportional to the square root of the intensity of the infrared light 324 detected by the infrared detector 326. Also as stated, the intensity of the infrared light 324 detected by the infrared detector 326 is proportional to $1/D^2$. From these two relationships, the period of the square-wave signal from the light-to-frequency converter 414 is proportional to the distance D, and is also directly correlated to the degree of expansion and contraction of the user's diaphragm. In turn, the period can be used to determine respiration rate and respiration depth, as described below.

A mode switch 430 is used by the user 140 to select an operational mode with associated respiration monitoring and feedback criteria, as discussed below. In the depicted embodiment, the mode switch 430 is a control knob, but other embodiments employ known input devices, such as keypads and switches. A start/stop button 434 is used to turn the respiration feedback monitor 110 on and off. A power source 438, shown as an AAA battery, supplies power to the respiration feedback monitor 110. The power source 438 is electrically coupled to a switching power supply 442 that ensures specified voltage and current levels to power the microcontroller 418. In the depicted embodiment, a voltage level of 3.3 VDC and a current level of 40 mA is used to power the microcontroller 418 and other components. The switching power supply 422 also includes a battery low output line 446 connected to the microcontroller 418 that alerts the microcontroller when the power source 438 has reached a state of low energy content.

A vibrator motor 450 with a weight 452 is used as a vibration output device to transmit vibrations, also know as a vibration signal, for feedback to the user 140. The microcontroller 418 controls the vibrator motor 450 on/off control line 454. Other embodiments of the invention also utilize output devices that transmit auditory and/or visual feedback signals to the user 140.

Respiration patterns, including respiration rate and depth, are stored by the microcontroller 418 in a data memory 458. The data memory 456 is electronically connected to the microcontroller 418 to store data and furnish instructions to the microcontroller. In the depicted embodiment data memory 456 comprises a 64×8 EEPROM, however, any other data and instruction storage device known in the art is contemplated for other embodiments with size being a restriction upon selection. In other embodiments, the microcontroller 418 is monolithically integrated with the data memory 456 on a single integrated circuit chip. In further embodiments, other combinations of the electrical components discussed are monolithically integrated with the microcontroller 418 on a single integrated circuit chip.

A computer interface cable connector 462 is detachably connected to the computer interface cable 230 and allows the microcontroller 418 to download data stored in the data memory 458 into a computer system 220. In an alternative embodiment, the respiration feedback monitor 110 uses the computer system 220 to provide feedback without using the vibrator motor 450 and the weight 452. In this alternative embodiment, the respiration feedback monitor 110 does not include the vibrator motor 450 and the weight 452 in the housing 120, so the respiration feedback monitor serves more as a portable data collection system. The computer interface cable connector 462 also allows various operational modes with their associated parameters and thresholds to be downloaded into the microcontroller 418 and the data memory 458 from a computer system 220. A status indicator 466, typically a red light, and a power indicator 470, typically a green light, convey status and power information discussed below to the user 140 about the current condition of the respiration feedback monitor 110. Devices other than lights, such as LED displays, audio output devices or other devices known in the art to convey status and power information, are used by other embodiments of the invention.

Figure 4B:
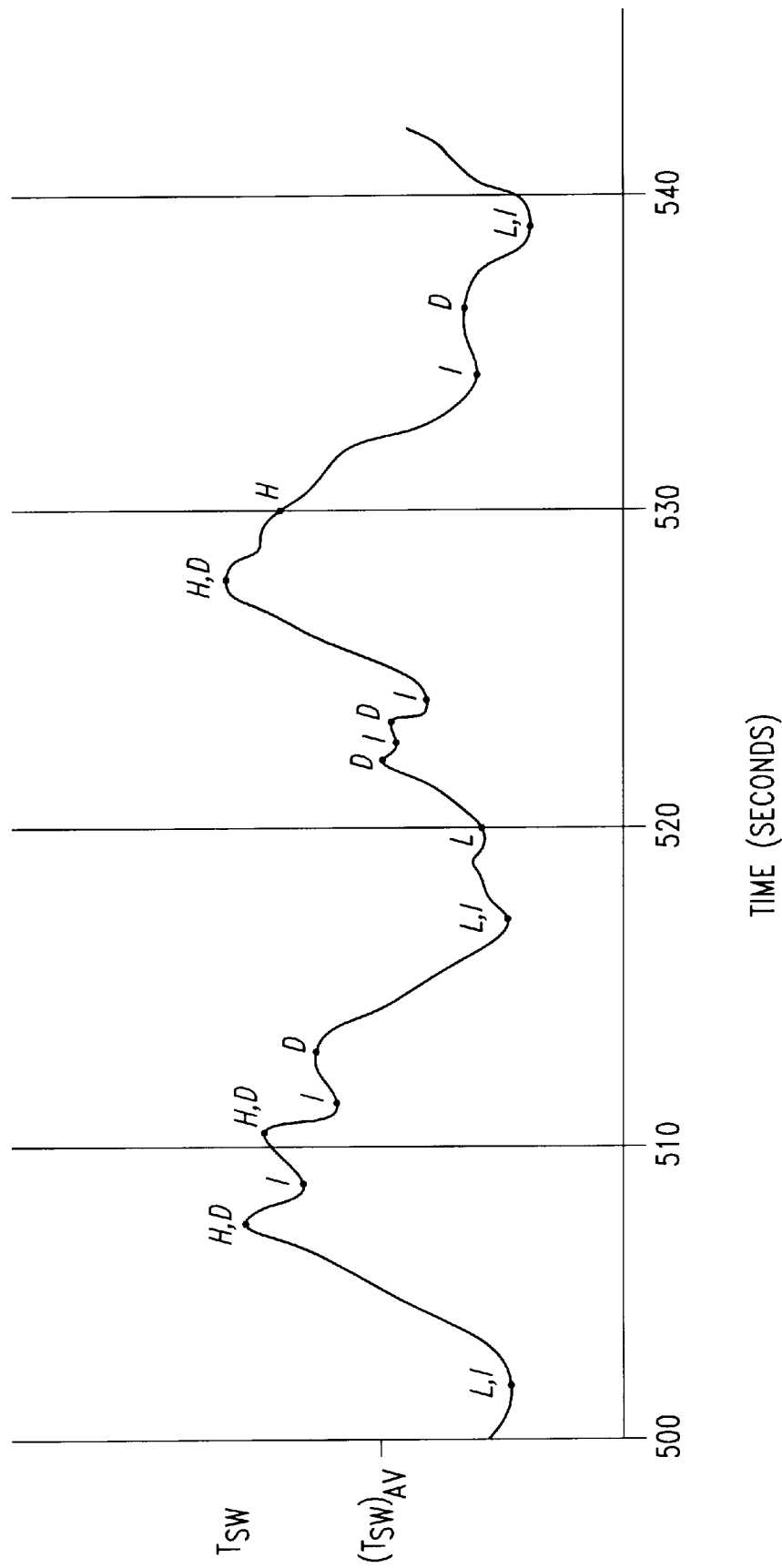
FIG. 4B is a plot of Square-Wave Period versus Time showing characteristics involved with breath measurement performed by the embodiment of FIG. 1.

Respiration rate and respiration depth are the two key respiration measurements performed by the respiration feedback monitor 110. Since the period $T_{SW}$ of the square-wave signal from the light-to-frequency converter 414 directly correlates to the amount of expansion and contraction of the diaphragm of the user 140, the respiration feedback monitor 10 determines respiration rate and respiration depth based on the period $T_{SW}$. In the depicted embodiment, initiation of a breath is defined to be the point where the period $T_{SW}$ becomes larger than a running average of the period $T_{SW}$. The microcontroller 418 determines the running average of the period $T_{SW}$ by storing a set of largest values for $T_{SW}$ and a set of smallest values for $T_{SW}$ into data memory 458. The running average would typically be over the most recent 5 to 10 minutes and result in each set having about a dozen values. The microcontroller 418 then takes a simple statistical average of these values. The microcontroller 418 then updates the two sets of largest and smallest values every certain period, typically every 10 seconds, as shown in FIG. 4B where the points "H" and "L" designate the high and low or large and small values of $T_{SW}$, respectively, for each 10 second period and $(T_{SW})_{AV}$ designates the running average for the period of collection up through 540 seconds of monitoring. In updating the two sets, the microcontroller 418 replaces the oldest of the one largest and smallest values with current largest and smallest values over the certain period. Direct replacement occurs unless the largest value is more than a certain percentage, typically 200%, of the largest value being replaced, which would indicate a possible error condition. Conversely, the smallest value is directly replaced unless the replacement value is less than a certain percentage, typically 50%, of the smallest value being replaced, also indicating a possible error condition. For the possible error conditions, the replacement value used will be a certain percentage of the most recently measured largest or smallest values.

Defining initiation of a breath as the point where the time period $T_{SW}$ becomes larger than the running average of the $T_{SW}$ time period, $(T_{SW})_{AV}$ of FIG. 4B, helps to eliminate erroneous measurements. In an alternative embodiment, initiation of a breath is defined in terms of whether the period $T_{SW}$ currently being measured has reached a peak by changing direction in increasing or decreasing value. In FIG. 4B, the peaks labeled "I" and "D" are points in time when $T_{SW}$ starts to increase and decrease in value, respectively. In this alternative embodiment, either the set of "I" or "D" peaks are used. As shown by FIG. 4B, this alternative embodiment, however, is prone to have more errors in measuring respiration rate and depth, because false peaks can be generated by such things as movements either of the respiration feedback monitor 110 or the user 140 or hesitations in breathing by the user. These false peaks are not the start of inhalation or exhalation in the user's breathing cycle so leads to errors. Also, the depicted embodiment uses a definition regarding initiation of a breath that allows the respiration feedback monitor 110 to consistently determine the current point of the breathing cycle so that feedback can be given at a precise moment relative to the breathing cycle.

The respiration feedback monitor 110 measures rate by measuring the time between two consecutive breath initiation points (i.e., a respiration cycle). The respiration feedback monitor 110 measures respiration depth for a particular respiration cycle by taking the difference between the maximum and minimum time periods $T_{SW}$ during the particular respiration cycle.

The criteria for proper feedback in general is to furnish only enough feedback to be corrective without being overly annoying. In practice, the amount of feedback required depends upon the particular user. Also, the precise moment when feedback is given during the breath cycle is dependent upon what corrective action is desired. The microcontroller 418 uses a variety of different criteria to tailor feedback appropriately to the individual user 140.

The vibrator motor 450 with weight 452 is activated by the microcontroller 418 to provide vibratory or tactile feedback to the user 140 when certain parameters are satisfied to generate a feedback event. Some of these parameters are downloaded into the data memory 458 to program the respiration feedback monitor 110. These parameters are selected from preselected parameters, such as time that the respiration rate or depth stays above a specified threshold, minimum and maximum threshold levels for respiration rate or depth to exceed and not to exceed, respectively, amount of time since the last feedback event, duration of feedback, percent of overall time that the respiration rate or depth is above a certain amplitude, and/or the amount of standard deviation or corrected standard deviation of the respiration rate or depth.

The user 140 selects entire sets of parameters with particular operational modes having individualized respiration feedback criteria with the mode switch 430. In this way, the respiration feedback monitor 110 can be used for different purposes or activity levels. For example, one setting would remind the user 140 not to hyperventilate when thinking about a particular stressful activity, such as an upcoming test. Another setting would assist the user in breathing properly while singing or giving a speech. A physician or therapist would preset some of these sets of parameters used based on clinical information, skill level of the user 140, and appropriate activity for the user 140. The therapist would then determine the appropriate setting and download several sets of parameters that would correspond to different rotary positions of the mode switch 430. The therapist would then instruct the user 140 regarding the settings of the mode switch 430. For instance, setting 1 could be used during studying, setting 2 could be used during singing, setting 3 could be used during resting, and setting 4 could be used during presenting a speech, setting 5 could be used for concentrating when playing golf, etc.

The sets of parameters are downloaded into the respiration feedback monitor 110 from the computer system 220 over the computer interface cable 230 into the respiration feedback monitor. These parameters are used by the microcontroller 418 to analyze the period $T_{SW}$ of the oscillating square-wave signal provided by the light-to-frequency converter 414. Depending on the results of the analysis by the microcontroller 418, the data memory 458 stores certain historical data on respiration activity of the user 140. Typically, the therapist indicates which data and statistics are stored in the data memory 458 during programming of the respiration feedback monitor 110 when the parameters are downloaded from the computer system 220 into the respiration feedback monitor via the computer interface cable 230.

The respiration feedback criteria including parameters stored in data memory 458 may also be modified by the microcontroller 418 directly based upon past activity of the user 140. For example, the user 140 may select with the mode switch 430 a certain percentage. The microcontroller 418 would then adjust feedback thresholds based on the user's past activity and the certain percentage selected by the user so that over the course of subsequent monitoring, feedback would be given only for a percentage of the time period equal to the certain selected percentage. The microcontroller 418 then adjusts and updates the threshold in order that feedback occurs at the selected percentage of time. For example, if the user selects feedback to occur on average of 25% for any given period of time, the microcontroller 418 would take previous recorded respiration activity and adjust the threshold so that the user was in the range of 75% of the time and out of range 25% of the time. The microcontroller 418 of the respiration feedback monitor 110 would then give the appropriate amount of feedback. If performance of the user 140 subsequently changes, the microcontroller 418 adjusts the threshold appropriately so that the amount of feedback would still be 25% on average of the overall time for monitoring.

Also, in the case of respiration depth, thresholds are based on measurements of the depth of respiration by the particular user 140 where the thresholds may relate for example to an average respiration depth of the user. Other examples of the microcontroller 418 adjusting feedback criteria based upon past activity of the user 140 include use of distribution plots including histograms to adjust feedback ratios as discussed below. These examples are only representative since in other embodiments of the invention the microcontroller 418 uses other functions including combinations of linear and non-linear functions based on past respiration rate and/or depth of the user 140 to directly adjust the respiration feedback criteria.

In the depicted embodiment, two basic feedback signals are available to alert the user 140. The first feedback signal, such as two short vibrational pulses, is to alert the user 140 to take a breath. If the user 140 is typically inhaling and then holding his or her breath, the feedback occurs during the part of the breath cycle right after inhalation to remind the user to exhale. If the user 140 is typically exhaling and then forgetting to inhale, the feedback is given at the beginning of the respiration cycle. The second feedback signal, such as one long vibrational pulse, is to slow down the breathing rate. Typically this would occur when an individual was taking quick shallow breaths. The second feedback signal in the depicted embodiment is given at the beginning of the breath cycle.

In the depicted embodiment there are three general approaches regarding feedback criteria that the microcontroller 418 uses to determine when respiration is improper and an additional feedback criteria to determine how often feedback should be given. These three main approaches for feedback criteria involve using a threshold, tracking an average, and using a distribution plot such as a histogram, which can be used alone or in combinations with one another. A threshold for respiration rate is typically selected by the therapist during an office visit by the user 140. The therapist uses the computer system 220 to analyze respiration patterns of the user 140. Based upon the analysis, the therapist then selects appropriate thresholds for maximum and/or minimum respiration rates. Here the thresholds for respiration rates are typically related to standard normative values associated with relatively healthy individuals.

A threshold for respiration depth under the first approach is typically based on average respiration depth generated by the user 140 as monitored with the respiration feedback monitor 110 and the computer system 220. Respiration depth is more specific to the particular user 140 than respiration rate. Once the averages for respiration depth are generated, the related thresholds for respiration depth are typically determined by a therapist using the computer system 220, and are downloaded into the data memory 458 of the respiration feedback monitor 110. For this first main approach, a feedback event occurs when the respiration rate or depth of the user 140 exceeds the related maximum threshold or goes below the minimum related threshold. The respiration feedback monitor 110 will then provide feedback to the user at an appropriate time.

A second approach for feedback criteria involves tracking average respiration rate or average respiration depth of the user 140. This approach is typical for situations when the user 140 relies solely on the respiration feedback monitor 110, without reliance on additional support from a clinic and/or the computer system 220. Here, the respiration feedback monitor 110 keeps a running average of the respiration rate or respiration depth of the user 140. For this second main approach, a feedback event occurs when the respiration rate or depth of the user strays beyond a certain percentage from the running average or if the running average goes above or below certain thresholds. The respiration feedback monitor 110 will then provide feedback to the user at an appropriate time.

A third approach for feedback criteria involves generating distribution plots such as histograms based on the respiration rate and/or respiration depth of the user 140. The distribution plot approach allows for some discrepancies regarding respiration rate or depth of the user 140 compared to a certain standard. In this sense, use of a distribution plot is more forgiving than other approaches, so that the user 140 is not overwhelmed by too many feedback events. In the distribution plot of the depicted embodiment a histogram is used. According to this histogram implementation of the distribution plot, N number of bins are allocated for a range of possible values, the possible values based upon an expression involving respiration rates and/or depths for the user 140. A bin is an abstract container that holds a count. For the depicted embodiment, the count is the number of occurrences when a measured value is one of a set of values. In the depicted embodiment, the measured value is breath rate and/or depth and the set of values is typically a range of possible breath rates and/or depths. For instance, for the depicted embodiment, one histogram involving values directly related to respiration rate uses 5 bins. The first through fifth bins are associated with the following ranges for breath rate BR: $0 \leq BR < 4$, $4 \leq BR < 6$, $6 \leq BR < 8$, $8 < BR < 12$, and $BR \leq 12$ breaths/minute, respectively. If for the last ten most recent breaths, the user 140 breathes at rates of 6, 10, 6, 7, 2, 10, 5, 7, 2, and 6 breaths/minute, respectively, two counts would be assigned to the first bin, four counts to the second bin, two counts to the third bin, two counts to the fourth bin, and 0 counts to the fifth bin. After updating the number of counts assigned to each bin, the microcontroller 418 normalizes each count so each bin count is expressed in terms of a percentage of the total number of counts. For the representative example above, the bin counts would be normalized to 20%, 40%, 20%, 20%, and 0% for the first through fifth bins, respectively. However, in other embodiments the values are based on expressions involving linear and/or non-linear functions of respiration rate and/or depth.

Typically, the microcontroller 418 keeps track of a most recent number (e.g. a dozen) of breaths. When the user 140 takes a breath, the microcontroller determines a value based on the respiration rate and/or depth involved and assigns a count to a specific bin associated with values including the determined value. The microcontroller 418 then discards the least recently assigned count from its associated bin to maintain twelve counts in the bins. The microcontroller 418 normalizes the counts assigned to the bins by converting the counts to percentages of the total of all counts assigned to all bins. The microcontroller 418 then compares the percentages for selected bins of the histogram to certain model percentages. The model percentages are either downloaded into the data memory 458 from the computer system 220 or are generated by the microcontroller 418 based on respiration data associated with the user 140 and recorded by the microcontroller into the data memory. Typically, the microcontroller 418 will check bins of a histogram that are at or near the maximum and minimum values of the histogram range. For this third approach, a feedback event occurs when one or more of these bins associated with the respiration of the user 140 have percentages that exceed the associated model percentages. The microcontroller will then furnish feedback at an appropriate time to the user. The effect of using the histogram is to shape the respiration patterns of the user 140 toward an ideal. This use of the histogram is essentially a first screening to check whether the respiration of the user is within an acceptable error limit.

In all three approaches for feedback criteria, the microcontroller 418 furnishes feedback to the user 140 at an appropriate time based on feedback events. However, the appropriate time for feedback may not be every time a feedback event occurs. The appropriate time to give feedback relates to both a precise moment in time relative to the current breath cycle of the user 140 and also relates to how often feedback has been given in the recent past. For instance, to encourage the user 140 to breathe, feedback is typically appropriate at the beginning of a current breath cycle. However, the amount or frequency of feedback that is appropriate varies depending on the particular individual, as discussed more fully below. For some individuals, even though a respiration event such as breaching a threshold has occurred, feedback would not be given if there has already been too much recent feedback for the individual. Too much feedback could be annoying or even detrimental for the desired therapeutic result.

In the depicted embodiment, the microcontroller 418 uses a second histogram of the respiration of the user 140 to determine an appropriate amount of feedback for a particular user 140. The second histogram of the user 140 may be the same histogram of the user 140 associated with the third approach for feedback criteria described above depending upon which approach or approaches for feedback criteria are being used by the microcontroller 418. As with the third approach for feedback criteria, the microcontroller 418 assigns a range of values to each bin of an M number of bins to develop this second histogram. The value ranges are related to linear and/or non-linear functions of respiration rate and/or depth. The microcontroller 418 updates this second histogram in a similar manner described above. A number (e.g., a dozen) of the user's most recent breaths are monitored for breath rate and/or breath depth. The microcontroller 418 determines a value for each breath based on the linear and/or non-linear functions of respiration rate and/or depth. The microcontroller 418 then assigns a count to the bin corresponding to the determined value for each breath. After which, the microcontroller 418 divides the bin counts for each bin by the total number of counts. The total number of counts is the number of most recent breaths monitored (e.g., a dozen). This results in percentage figures for each bin to normalize the second histogram.

The microcontroller 418 then performs a correlation comparison of the normalized second histogram with a normalized ideal histogram (described below) upon each update to determine a correlation value. Although other correlation methods are used in other embodiments, the depicted embodiment uses a correlation method involving a difference method to determine the correlation value. Under the difference method, for at least one bin of the second histogram and up to all bins of the second histogram, the microcontroller 418 determines a difference between the percentages associated with a bin of the second histogram and the corresponding bin of the ideal histogram. The ideal histogram typically has the same number of bins as the second histogram and the bins of the ideal histogram are associated with the same values as the bins of the second histogram. Once the microcontroller 418 determines a difference for each bin pair compared, the microcontroller then adds all the differences to get a total. Before adding the differences, in one embodiment, the microcontroller weights the differences so that the differences associated with some bin pairs (e.g., the bins closer to the extremes of the histogram range) impact the total more than other differences of other bin pairs. The number resulting from totaling the weighted or unweighted differences is the correlation total and is then compared with a previous correlation total determined for a previous breath. In the depicted embodiment, the previous correlation total is for the most recent past breath.

The microcontroller 418 determines the difference between the previous correlation total and the current correlation total to determine respiration trend of the user 140. If the respiration trend of the user 140 is positive, the respiration of the user is getting closer to an ideal respiration (and ideal histogram) and the current correlation total will be smaller than the previous correlation total. As the user's respiration improves, the user requires less feedback than if the respiration of the user was staying the same or getting worse.

The microcontroller 418 factors improvement into how often feedback is generated. Thus, the microcontroller 418 may not give feedback to the user 140 every time a feedback event occurs. If the user 140 is dramatically improving, as shown by the continued reduction in correlation totals, the microcontroller 418 gives feedback to the user 140 only after a certain number of feedback events.

The number of feedback events per feedback given is preferably dependent on particular individuals. Some individuals are highly sensitive to feedback and require very little feedback. For these sensitive individuals, even when progress was non-existent, feedback may be appropriate for every certain number of feedback events. The amount of feedback given relative to the number of feedback events that occur is dependent upon the sensitivity of the individual user 140. Therefore, in the depicted embodiment, this sensitivity is programmed into the respiration feedback monitor 110, typically by downloading a set of ratios of amount of feedback given to number of feedback events that occur for various values of correlation totals and values of respiration trend. The microcontroller 418 would then select from the set of ratios the particular ratio that corresponds to the current correlation total and respiration trend of the user 140. The microcontroller 418 uses this selected ratio to determine an appropriate amount of feedback to give to the user 140. This ratio is updated as the current correlation total and respiration trend change.

The ideal histogram used in the correlation comparison typically is associated with model respiration patterns of human beings, so would usually have certain minor discrepancies compared to a theoretically ideal respiration. Depending upon the type of activity involved with respiration training, the ideal histogram may be generated by recording respiration rate and/or depth of an outstanding performer or leader in the field associated with the activity. For example, ideal histograms could be generated from model respiration patterns of outstanding surgeons performing delicate operations, tour-leading golfers as they produce a stellar putt or drive, or popular speakers as they deliver an inspiring speech, for surgical, golfing and public speaking applications, respectively. Other applications or fields of activity and persons involved are anticipated by other embodiments of the invention.

One aspect of the invention using successful leaders in a given activity is that the model respiration patterns are less than a theoretically ideal, but are as best as can be expected and are tailored for the activity. For instance, public speaking places great demands upon the speaker to maintain ideal respiration to the point that truly ideal respiration is not possible. Successful public speakers, however, have adapted their respiration to approach an ideal pattern while accommodating the demands of the activity.

The respiration feedback monitor 110 in other embodiments operates under other operational modes, including Percent Time Amplitude, Threshold Amplitude, Median Frequency, Prompted Exercise, and Current Breath Frequency Mode, each described below. Each mode can be operated either with fixed or adaptive thresholds. Adaptive thresholds change based on how the user progresses with his or her training. In the Percent Time Amplitude Mode, the microcontroller 418 determines the respiration depth of each breath over a predetermined period of time and discards the highest and lowest 5% of values for the time period. The remaining highest value is then set to be 100% amplitude. The range from the remaining highest and remaining lowest value is divided into N number of bins (e.g., 4). Each breath amplitude is assigned to the corresponding bin, showing the percent of time spent at each amplitude. Feedback is given based on the percentage levels in a preselected bin or bins. The thresholds associated with each percentage distribution for each selected bin are independently adjustable.

For the Threshold Amplitude Mode, the microcontroller 418 measures respiration depth of each breath and calculates a running average of respiration depth over a predefined number of breaths. This mode is useful for cases including where respiration rate should be slowed down even though measured respiration rate may be zero as is found with a hyperventilating individual. During hyperventilation, oftentimes an individual chest pants without moving their diaphragm to any appreciable degree. Typically the respiration feedback monitor 110 is secured around the diaphragm area, so does not appreciably measure movement of the chest area. The respiration depth component of this mode helps the respiration feedback monitor 110 recognize this particular situation and provide appropriate feedback.

This mode is also suitable where the size or configuration of the user 140 hinders measurement of respiration rate to a certain degree. The predefined number is a parameter that a therapist or user downloads into the data memory 458 or is factory set into the data memory. The microcontroller 418 calculates two threshold values based on the running average. The thresholds are fixed percentages of the running average. One threshold is a certain percentage above the running average. The other threshold is a percentage below the running average. The value of the fixed percentage is a preselected value, downloaded into the data memory 458 from the computer system 220 or is factory set into the data memory. The respiration feedback monitor 110, measures each new breath against the thresholds. If either threshold is exceeded within a certain preselected time period feedback is generated by the respiration feedback monitor 110. Also, the repetition or duration of vibration in one embodiment is linearly correlated to the amount that the respiration signal amplitude exceeds a threshold. For example, when the threshold is exceeded by 200%, feedback is given twice as often or will last twice as long as when threshold is exceeded by 100%.

In the Threshold Median Frequency Mode, the microcontroller 418 determines respiration rate of the user 140 as discussed above. The microcontroller 418 uses the current respiration rate to update a median rate by calculating a median of the respiration rates associated with the last N number of breaths. The microcontroller 418 then compares this current median value for respiration rate to maximum and minimum threshold values and signals for a feedback vibration to be generated if either threshold is breached. The threshold values are typically predetermined percentages above and below the median value.

For the Prompted Exercise Mode, the user 140 is prompted to begin exercising with a vibration of short duration. The degree of success is then signaled by other vibratory patterns. For example, a patient who needs to practice controlled breathing may go to a therapist. The therapist may determine that the patient should practice breathing at a certain rate and/or amplitude for a period of time. The therapist then downloads a set of rate and/or amplitude and time period parameters into the data memory 458 and assigns the set of parameters to switch position 1 of the mode switch 430.

Before an exercise session, the user then selects switch position 1 of the mode switch 430. At the beginning of the exercise session, the user 140 receives a single vibration from the vibratory motor 450 signaling the user to start the particular breathing exercise. During the exercise session the respiration feedback monitor 110 sends different vibrations to the user 140 to inform the user whether the user's respiration pattern is proper. For instance, the user may breath during the exercise session too rapidly or too slowly or the breaths taken may be too deep or shallow. In these cases, the respiration feedback monitor 110 sends unique vibration patterns of various unique singular vibrations or combinations of vibrations of long or short duration to signal the user of their improper respiration. When the exercise session is near or at completion, the respiration feedback monitor 110 alerts the user 140 with other unique vibration patterns. Data related to exercise sessions are saved in the data memory 458 for future reference by the therapist.

In the Current Breath Frequency Mode, the respiration feedback monitor 110 compares respiration rate of the user 110 to either a predetermined value (e.g., 20 breaths/minute) or the median frequency described above. In the case of the predetermined value, if the respiration rate of the user 110 exceeds the predetermined value, the respiration feedback monitor 110 generates a vibration pattern to be received by the user 140. In the case of the median frequency, a vibration is generated to be received by the user 140 if the respiration rate of the user is above or below the median frequency by a certain percentage. Comparison of the respiration rate of the user 140 to the median frequency acts as a shaping function that moves over time to force the current respiration rate of the user 140 closer to the user's previous respiration rate.

In the Depth Versus Time Mode, the microcontroller 418 determines current slopes of respiration depth versus elapsed time. When the user 140 gasps for air, the slope of respiration depth versus elapsed time will have an abnormally high value. In the case where the user 140 gasps for air and then holds his or her breath, the respiration rate may appear normal whereas the Depth Versus Time Mode will instead help determine that an unsatisfactory condition exists.

The various modes and approaches for determining appropriate moments and amounts of feedback are only representative examples of how the microcontroller 418 is configured to provide appropriate feedback. Other settings, thresholds, and other combinations of modes, approaches and functions involving respiration rate and/or depth are also included within the scope of the invention.

In the depicted embodiment, a procedure implemented in the microcontroller 418 of the respiration feedback monitor 110 to monitor respiration activity of the user 140 and provide appropriate feedback is illustrated in FIGS. 5A and 5B. The procedure starts at step 510, and proceeds to a sleep mode in step 512. In the sleep mode, the respiration feedback monitor 110 requires a minimal amount of power from the power source 438. Little measurement and analysis activity is done in the sleep mode by the respiration feedback monitor 110. In the sleep mode, the microcontroller 418 wakes up every two to three seconds, as depicted by a decision step 514. If the microcontroller 418 is to remain asleep, the procedure branches under the "no" condition back to the sleep mode (step 512). However, if the microcontroller is to wake up, the procedure branches under the "yes" condition to a decision step 516.

In decision step 516, the microcontroller checks the condition of the start/stop button 434 as indicated by an internal register to see if any conditions have occurred since the microcontroller had last checked status of the start/stop button. If a stop condition has occurred, the procedure branches under the "no" condition back to the sleep mode (step 512). If a start condition has occurred, the procedure branches under the "yes" condition to a step 518. In step 518, the green status indicator 466 and red power indicator 470 lights are flashed to indicate that the respiration feedback monitor has been activated.

The procedure then goes to a step 520 where the microcontroller 418 performs tests, including checking battery voltage and downloading all necessary parameters from the data memory 458 according to the setting of the mode switch 430. If the tests in step 520 are not performed in a certain amount of time, then a decision step 522 branches under the "yes" condition to a step 524 where the red power indicator light 470 and the green status indicator light 466 are turned off and the procedure goes back to the sleep mode step 512. If a timeout condition has not occurred in decision step 522, the procedure branches under the "no" condition to a decision step 526 where it is determined whether all the tests have been passed. If not all the tests have been passed, the decision step 526 branches under the "no" condition to a step 528, where the green status light 466 is turned off, and the red power indicator light 470 remains on. Step 528 then goes back to step 520, where further tests are performed.

If it is determined in decision step 526 that all tests have been passed, the procedure branches under the "yes" condition to an initialization step 530 where the microcontroller performs an initialization step. During initialization, the microcontroller 418 starts to provide power to the infrared emitter 322 and the light-to-frequency converter 414. After the initialization step 530, the procedure goes to a step 532, where the green status indicator light 466 and red power indicator light 470 are set with predefined flashing frequency to indicate that the respiration feedback monitor 110 is in operational mode.

The procedure then goes to a step 534, where output data from the light-to-frequency converter 414 is sampled, and then analyzed and stored in a step 536, by the microcontroller 418. In a decision step 538, the microcontroller 418 determines whether a certain amount of time has elapsed. If not, the decision step 538 branches under the "no" condition back to step 534 where more data is sampled. If a certain amount of time has passed, decision step 538 branches under the "yes" condition to a decision step 540, where the microcontroller 418 determines whether feedback is appropriate.

If feedback is appropriate, the procedure branches under the "yes" condition to a step 542, where the vibrator motor 450 is turned on by the microcontroller 418 to send a vibration signal to the user 140. If feedback is not appropriate, the decision step 540 branches under the "no" condition to a decision step 544, where the microcontroller determines whether the mode switch 430 has changed, since a previous determination under decision step 544 was made.

If the mode switch 530 has changed, the decision step 544 branches under the "yes" condition back to step 530, where the microcontroller 418 again performs initialization. If the mode switch 530 has not changed, the decision step 544 branches under the "no" condition to a decision step 546 where the microcontroller 418 determines whether the respiration feedback monitor 110 is still being used. The microcontroller 418 can determine whether the respiration feedback monitor 110 is still in use by characteristic patterns of the output from the light-to-frequency converter 414. If the microcontroller 418 determines that the respiration feedback monitor 110 is still in use, then the decision step 546 branches under the "yes" condition back to step 534, where more data is sampled by the microcontroller 418; otherwise, the decision step 546 branches under the "no" condition back to the sleep mode step 512.

All of the above U.S. patents and applications are incorporated by reference. While the depicted embodiment is used in training and rehabilitation for health conditions, other embodiments of the invention can similarly be used for monitoring and providing feedback related to other objectives, such as, for example, sports related activities, scientific research, business activities, or for use with animals, such as for training. Furthermore, aspects of the embodiments disclosed in the commonly assigned, copending U.S. applications referenced above can be combined with aspects of the embodiments disclosed herein. For instance, aspects of the Electromyographic Feedback Monitor System could be combined with aspects disclosed herein resulting in a feedback monitor for a user's muscle and respiration activities. As an alternative example, aspects of the Heart Rate Variability Feedback Monitor System could be combined with aspects disclosed herein resulting in a feedback monitor for a user's heart and respiration activities.

These and other changes can be made to the invention in light of the above detailed description. In general, in the following claims, the terms should not be construed to limit the invention to specific embodiments disclosed in the claims, but should be construed to include all wearable respiration feedback monitors that operate under the claims to provide a wearable system for monitoring and providing appropriate feedback related to respiration activity of the user, and to all feedback systems operating under one or more of the above methods. Accordingly, the invention is not limited by the disclosure, but instead its scope is to be determined entirely by the following claims.

What is claimed is:

1. A respiration monitor system comprising:

a housing sized and configured to be worn by a user;

a vibration output device affixed to the housing, the vibration output device configured to transmit a vibration signal perceptible by the user when the vibration output device is activated;

a non-rigid member configured to extend and retract with respect to at least a portion of the housing, to correspond to respiration of the user;

a signal generator affixed to the housing, the signal generator configured to generate distance signals indicating a distance related to the extension and retraction of the non-rigid member;

a memory configured to store respiration feedback criteria;

a processor affixed to the housing and coupled to the memory, the vibration output device and the signal generator, the processor configured to receive the distance signals and configured to turn on the vibration output device based on whether the distance signals satisfy the stored respiration feedback criteria; and a mode switch wherein the user with the mode switch selects an operational mode having a particular respiration feedback criteria from a plurality of operational modes under which the processor operates wherein the processor is further configured to adjust the respiration feedback criteria of the selected operational mode based on the distance signals.

2. A respiration monitor system comprising:

a housing sized and configured to be worn by a user;

a vibration output device affixed to the housing, the vibration output device configured to transmit a vibration signal perceptible by the user when the vibration output device is activated;

a non-rigid member configured to extend and retract with respect to at least a portion of the housing, to correspond to respiration of the user;

a signal generator affixed to the housing, the signal generator configured to generate distance signals indicating a distance related to the extension and retraction of the non-rigid member;

a memory configured to store respiration feedback criteria;

a processor affixed to the housing and coupled to the memory, the vibration output device and the signal generator, the processor configured to receive the distance signals and configured to turn on the vibration output device based on whether the distance signals satisfy the stored respiration feedback criteria; and a mode switch wherein the user with the mode switch selects an operational mode having a particular respiration feedback criteria from a plurality of operational modes under which the processor operates wherein the plurality of operational modes comprises: Percent Time Amplitude Mode, Threshold Amplitude Mode, Media Frequency Mode, Prompted Exercise Mode, or Current Breath Frequency Mode.

3. A respiration monitor system comprising:

a housing sized and configured to be worn by the user;

an output device affixed to the housing, the output device configured to transmit a signal perceptible by the user when the output device is activated;

a processor affixed to the housing, the processor configured to receive distance signals and configured to activate the output device based on whether the distance signals satisfy a respiration feedback criteria to signify a feedback event; and a signal generator affixed to the housing, the signal generator configured to generate the distance signals indicating distances varying with an extent of expansion and contraction of the user during respiration by the user, the signal generator comprising a light receiver configured to receive reflected light and a light reflector configured to reflect light to the light receiver, the light reflector configured to reflect light to the light receiver with an intensity based upon the extent of expansion and contraction of the user, the signal generator configured to generate the distance signal, based upon the intensity of the reflected light received by the light receiver.

4. A respiration monitor system comprising:

a housing sized and configured to be worn by the user;

an output device affixed to the housing, the output device configured to transmit a signal perceptible by the user when the output device is activated; and a processor affixed to the housing, the processor configured to receive distance signals and configured to activate the output device based on whether the distance signals satisfy a respiration feedback criteria to signify a feedback event wherein the respiration feedback criteria are related to distance signal measurements and time measurements associated with the distance signals.

5. A respiration monitor system comprising:

a housing sized and configured to be worn by the user;

an output device affixed to the housing, the output device configured to transmit a signal perceptible by the user when the output device is activated; and a processor affixed to the housing, the processor configured to receive distance signals and configured to activate the output device based on whether the distance signals satisfy a respiration feedback criteria to signify a feedback event wherein the respiration feedback criteria are associated with a threshold, tracking an average, or using a histogram.

6. A respiration monitor system comprising:

a housing sized and configured to be worn by the user;

an output device affixed to the housing, the output device configured to transmit a signal perceptible by the user when the output device is activated; and a processor affixed to the housing, the processor configured to receive distance signals and configured to activate the output device based on whether the distance signals satisfy a respiration feedback criteria to signify a feedback event, the processor being further configured to turn on the vibration output device based on present correlation results compared with past correlation results wherein the past and present correlation results are based on correlations of a histogram of values associated with the distance signals correlated with an ideal histogram.

7. A respiration monitor system comprising:

a housing sized and configured to be worn by the user;

an output device affixed to the housing the output device configured to transmit a signal perceptible by the user when the output device is activated; and a processor affixed to the housing, the processor configured to receive distance signals and configured to activate the output device based on whether the distance signals satisfy a respiration feedback criteria to signify a feedback event, the processor being further configured to adjust the respiration feedback criteria based on the distance signals.

8. A respiration monitor system comprising:

a housing sized and configured to be worn by the user;

an output device affixed to the housing, the output device configured to transmit a signal perceptible by the user when the output device is activated; and a processor affixed to the housing, the processor configured to receive distance signals and configured to activate the output device based on whether the distance signals satisfy a respiration feedback criteria to signify a feedback event wherein the processor has a low power sleep mode and a higher power operational mode.

9. A respiration monitor system comprising:

a housing sized and configured to be worn by the user;

an output device affixed to the housing, the output device configured to transmit a signal perceptible by the user when the output device is activated; and a processor affixed to the housing, the processor configured to receive distance signals and configured to activate the output device based on whether the distance signals satisfy a respiration feedback criteria to signify a feedback event wherein the distance signals are generated based upon a measured light intensity.

10. A respiration monitor system comprising:

a housing sized and configured to be worn by the user;

an output device affixed to the housing, the output device configured to transmit a signal perceptible by the user when the output device is activated; and a processor affixed to the housing, the processor configured to receive distance signals and configured to activate the output device based on whether the distance signals satisfy a respiration feedback criteria to signify a feedback event wherein the processor determines respiration patterns of the user including respiration rates, respiration depths, and associated time measurements.

11. A respiration monitor system comprising:

a housing sized and configured to be worn by the user;

an output device affixed to the housing, the output device configured to transmit a signal perceptible by the user when the output device is activated; and a processor affixed to the housing, the processor configured to receive distance signals and configured to activate the output device based on whether the distance signals satisfy a respiration feedback criteria to signify a feedback event wherein the processor is configured to process a plurality of operational modes comprising Percent Time Amplitude Mode, Threshold Amplitude Mode, Median Frequency Mode, Prompted Exercise Mode, or Current Breath Frequency Mode.

12. A respiration monitor system comprising:

a housing configured to be worn by the user;

a storage device affixed to the housing, the storage device configured to store data related to respiration;

a communication link configured to provide signals from the respiration feedback monitor system to a computer system wherein the data related to respiration is transferred to the computer system; and a processor affixed to the housing configured to receive distance signals associated with the respiration data, the processor configured to transmit a signal to an output device based on the distance signals and respiration feedback criteria, the respiration feedback criteria received from the computer system via the interface cable and connector wherein the computer system is configured to adjust the respiration feedback criteria.

13. A respiration monitor system comprising:

a housing configured to be worn by the user;

a storage device affixed to the housing, the storage device configured to store data related to respiration;

a communication link configured to provide signals from the respiration feedback monitor system to a computer system wherein the data related to respiration is transferred to the computer system;

a processor affixed to the housing, the processor configured to receive distance signals associated with the respiration data, the processor configured to transmit a signal to an output device based on the distance signals and respiration feedback criteria received from the computer system; and a connector configured to detachably connect the respiration feedback monitor system to a computer system wherein the computer system is configured to transfer parameters associated with a plurality of operational modes to the storage device, the processor performing according to the parameters associated with at least one of the operational modes.

14. A respiration monitor system comprising:

a housing configured to be worn by the user;

a storage device affixed to the housing, the storage device configured to store data related to respiration;

a communication link configured to provide signals from the respiration feedback monitor system to a computer system wherein the data related to respiration is transferred to the computer system; and a mode switch wherein the user selects with the mode switch an operational mode from the plurality of operational modes stored in the storage device, the processor performing according to the parameters associated with the selected operational mode.

15. A respiration monitor system comprising:

a housing configured to be worn by the user;

a processor affixed to the housing configured to receive distance signals associated with respiration events of the user, the processor configured to turn on an output device based on respiration feedback criteria associated with the distance signals; and a communication link configured to provide signals from a system computer to the respiration monitor system to a computer system wherein the computer system is configured to adjust the respiration feedback criteria wherein the respiration feedback criteria includes Percent Time Amplitude Mode, Threshold Amplitude Mod, Medium Frequency Mode, Prompted Exercise Mode, or Current Breath Frequency Mode.

16. A method comprising:

assigning parameter values for a plurality of operational modes associated with a respiration feedback monitor system;

selecting an operational mode from the plurality of operational modes;

generating respiration signals associated with respiration activity of the user;

analyzing the respiration signals based on an operational mode; and transmitting a signal perceptible by the user based upon results of the analysis.

17. The method of claim 16 wherein assigning or analyzing is performed remote to where generating is performed.

18. The method of claim 16, further including:

adjusting respiration feedback criteria associated with the plurality of operational modes based upon results of the analysis.

19. The method of claim 16 wherein the transmitted signal is a vibration signal.

20. A method of generating feedback for a user, the method comprising:

taking measurements related to at least one physical parameter associated with the user;

establishing feedback criteria defining a feedback event based on the measurements;

generating a histogram based on the measurements;

correlating the histogram with an ideal histogram;

comparing the correlation with past correlations to determine a trend; and generating an amount of feedback for the user, the amount of feedback dependent upon the measurements, the feedback criteria, and the trend.

21. The method of claim 20 wherein the feedback event relates to a second histogram based on the measurements.

22. The method of claim 20 wherein the physical parameter depends upon the user's respiration.

23. A feedback system for a user, the system comprising:
- a sensor configured to transmit signals based upon a physical parameter associated with the user;
- a memory storing a distribution plot and feedback criteria; and
- a processor coupled to the probe member to receive the signals, and coupled to the memory, the processor configured to determine a measurement involving the physical parameter associated with the user based upon the received signal, wherein the processor is configured to generate a distribution plot based on the determined measurements, the processor is configured to calculate a correlation between the generated distribution plot and the distribution plot stored in the memory, the processor is configured to determine a feedback event based upon the determined measurements and the stored feedback criteria, wherein the processor is configured to establish a trend based upon a comparison between the calculated correlation and previous correlations, and wherein the processor is configured to generate feedback to the user based upon the measurements, the feedback criteria, and the trend.

24. The feedback system of claim 23 wherein the feedback event relates to a second distribution plot based on the determined measurements.

25. The feedback system of claim 23 wherein the physical parameter depends on the user's respiration.

26. The feedback system of claim 23 wherein the stored distribution plot represents a model respiration pattern.

27. The feedback system of claim 23 wherein the processor and memory are monolithically integrated on the same integrated circuit.

28. The feedback system of claim 23 wherein the generated and stored distribution plots are histograms.

* * * * *

UNITED STATES PATENT AND TRADEMARK OFFICE
CERTIFICATE OF CORRECTION

PATENT NO. : 6,162,183
DATED : December 19, 2000
INVENTOR(S) : Jan C. Hoover

It is certified that error appears in the above-identified patent and that said Letters Patent is hereby corrected as shown below:

Column 20, claim 7,
Line 33, "housing the output" should read -- housing, the output --.

Column 22, claim 15,
Lines 27 and 28, "Threshold Amplitude Mod," should read -- Threshold Amplitude Mode, --.

Signed and Sealed this

Twentieth Day of November, 2001

Attest:

NICHOLAS P. GODICI
*Attesting Officer*     *Acting Director of the United States Patent and Trademark Office*